(12) United States Patent
Brieden et al.

(10) Patent No.: US 6,716,999 B2
(45) Date of Patent: Apr. 6, 2004

(54) PYRONE DERIVATIVES AND METHOD FOR PRODUCING SAME

(75) Inventors: Walter Brieden, Brig-Glis (CH); Michael Gottsponer, Visperterminen (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/148,190

(22) PCT Filed: Dec. 6, 2000

(86) PCT No.: PCT/EP00/12243

§ 371 (c)(1),
(2), (4) Date: Aug. 12, 2002

(87) PCT Pub. No.: WO01/40212

PCT Pub. Date: Jun. 7, 2001

(65) Prior Publication Data

US 2003/0013896 A1 Jan. 16, 2003

Related U.S. Application Data

(60) Provisional application No. 60/185,368, filed on Feb. 28, 2000.

(30) Foreign Application Priority Data

Dec. 6, 1999 (EP) .............................. 99124350

(51) Int. Cl.⁷ ...................... C07D 309/32; C07D 315/00

(52) U.S. Cl. ....................................................... 549/423
(58) Field of Search .......................................... 549/423

(56) References Cited

U.S. PATENT DOCUMENTS

| | | | |
|---|---|---|---|
| 3,937,737 A | 2/1976 | Eiglmeier | |
| 4,082,807 A | 4/1978 | Eiglmeier | |

FOREIGN PATENT DOCUMENTS

| | | |
|---|---|---|
| CA | 1071236 | 2/1980 |
| CH | 602 542 A | 12/1977 |
| DE | 2451006 A | 4/1976 |
| FR | 2238696 A | 7/1974 |

OTHER PUBLICATIONS

Lowe, Werner, J. of Heterocyclic Chemistry, vol. 34, No. 4, (Jul. 1997), pp. 1173 to 1178, (Lowe).

Kawada, A., et al., Synlett, Thieme Verlag, (Jul. 1, 1994), pp. 545 and 546.

*Primary Examiner*—Taofiq Solola
(74) *Attorney, Agent, or Firm*—Fisher, Christen & Sabol

(57) ABSTRACT

A method for producing pyrone derivatives of the general formula (I), wherein $X^1$ is halomethyl, whereby an acetoacetic acid derivative of the general formula (II), wherein $X^1$ has the aforementioned meaning and $X^2$ is chlorine or bromine, is treated with a Lewis acid and is subsequently converted into the desired product by means of water.

10 Claims, No Drawings

PYRONE DERIVATIVES AND METHOD FOR PRODUCING SAME

This is a 371 of International Application No. PCT/EP00/12243, filed on Dec. 6, 2000, that has benefit of U.S. Provisional Application Ser. No. 60/185,368, filed on Feb. 28, 2000, and that has priority benefit of European Patent Application No. 99124350.2, filed on Dec. 6, 1999.

The present invention relates to novel pyrone derivatives of the general formula

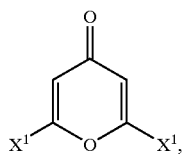

in which $X^1$ is halomethyl, with the exception of monobromomethyl and dibromomethyl, and a process for their preparation.

Pyrone derivatives of the general formula I such as, for example, 2,6-bis(chloromethyl)-4-pyrone can be important intermediates for the preparation of crown ethers (W. Löwe et al., *J. Heterocyclic Chem.*, 34, 1173 (1997)).

Until now, only 2,6-bis(bromomethyl)-4-pyrone and 2,6-bis(dibromomethyl)-4-pyrone and a process for their preparation were known (Löwe et al., ibid). In this process, 2,6-dimethyl-4-pyrone is brominated using N-bromosuccinimide/dibenzoyl peroxide in tetrachloromethane. A disadvantage of this process is that a mixture of various products is obtained, from which the said compounds can only be isolated in very low yield.

The object of the present invention was therefore to make available compounds which are suitable for the synthesis of crown ethers and a process for their preparation.

According to the invention, this object is achieved by the preparation method according to claim 1 and the novel pyrone derivatives according to claim 6.

The process according to the invention for the preparation of the pyrone derivatives of the general formula

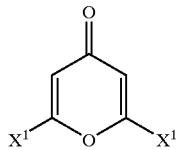

in which $X^1$ is halomethyl is carried out by treating an acetoacetic acid derivative of the general formula

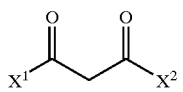

in which $X^1$ has the meaning mentioned and $X^2$ is chlorine or bromine, first with a Lewis acid and then converting it into the desired product of the general formula I using water.

Halomethyl is understood here and below as meaning trihalomethyl, dihalomethyl or monohalomethyl. In this case, trihalomethyl and dihalomethyl may contain both identical and different halogen atoms. Examples of trihalomethyl are trifluoromethyl and tribromomethyl, examples of dihalomethyl are dichloromethyl, dibromomethyl, difluoromethyl and examples of monohalomethyl are fluoromethyl, chloromethyl, bromomethyl or iodomethyl. Suitable halomethyl is, for example, also difluoromonochloromethyl, dibromomonochloromethyl and dichloromonofluoromethyl.

Suitable Lewis acids are scandium salts such as, for example, scandium trifluoromethanesulphonate, scandium sulphate, lanthanide salts such as, for example, lanthanum trifluoromethanesulphonate, yttrium salts or $BF_3 \cdot O(C_2H_5)_2$. The Lewis acid preferably employed is scandium trifluoromethanesulphonate.

The Lewis acid is advatageously employed in an amount from 0.01 to 3 mol, preferably in an amount from 0.05 to 0.5 mol, per mole of acetoacetic acid derivative of the general formula II.

The reaction is preferably carried out in a halogenated organic solvent. Halogenated organic solvents which can be employed are halohydrocarbons such as dichloromethane, chloroform, tetrachloromethane, 1,1,1-trichloroethane or 1,2-dichloroethane. Dichloromethane is particularly preferred.

The reaction is expediently carried out at a temperature of −20 to 60° C., preferably at a temperature of 0 to 25° C.

The reaction in the first and second stage is expediently carried out under an inert gas atmosphere such as, for example, under a nitrogen atmosphere.

After a customary reaction time of 1 to 8 days, the pyrone derivatives of the general formula I can be isolated by means of customary working-up methods.

The pyrone derivatives of the general formula I

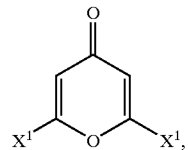

in which $X^1$ is halomethyl, with the exception of 2,6-bis(bromomethyl)-4-pyrone and 2,6-bis(dibromomethyl)-4-pyrone ($X^1$=bromomethyl or dibromomethyl), are novel compounds and likewise form subject-matter of the invention. Preferred pyrone derivatives of the general formula I are 2,6-bis(chloromethyl)-4-pyrone, 2,6-bis(fluoromethyl)-4-pyrone, 2,6-bis(iodomethyl)-4-pyrone, 2,6-bis(trifluoromethyl)-4-pyrone, 2,6-bis(tri-chloromethyl)-4-pyrone, 2,6-bis(tribromomethyl)4-pyrone, 2,6-bis(triiodomethyl)-4-pyrone and 2,6-bis(difluoromonochloromethyl)-4-pyrone.

A further subject-matter of the invention is the preparation of acetoacetyl derivatives of the general formula

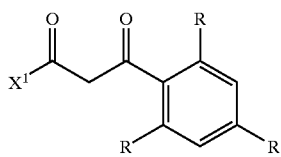

in which $X^1$ has the meaning mentioned and R is a $C_{1-6}$-alkyl group. Some compounds of this type are disclosed in CH-A-602 542. However, the synthesis described there is carried out in anhydrous hydrogen fluoride and is problematical owing to the corrosiveness and toxicity of the said compound.

According to the invention, an acetoacetic acid derivative of the general formula

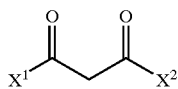

in which $X^1$ and $X^2$ have the meaning mentioned, is converted in the presence of a Lewis acid using a benzene derivative of the general formula

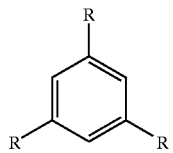

in which R is a $C_{1-6}$-alkyl group, into the final product according to formula III.

$C_{1-6}$-Alkyl is understood here and below as meaning both linear and branched alkyl groups having up to 6 carbon atoms such as, for example, methyl, ethyl, propyl, isopropyl, butyl, isobuyl, tert-butyl, pentyl and its isomers and hexyl and its isomers.

This reaction is advantageously carried out at a temperature of 20 to 30° C.

Scandium trifluoromethanesulphonate is preferably used as Lewis acid.

After a customary reaction time of about 2 days, the acetoacetyl derivatives of the general formula III can be isolated by customary working-up methods.

The acetoacetyl derivatives of the general formula

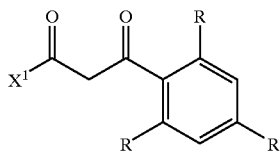

in which $X^1$ has the meaning mentioned and R is a $C_{1-6}$-alkyl, with the exception of γ-bromoacetoacetylmesitylene and γ,γ,γ-trichloro-acetoacetylmesitylene, are novel compounds and likewise form subject-matter of the present invention. The examples below illustrate the implementation of the process according to the invention and the preparation of the inventive compounds.

EXAMPLE 1

Preparation of 2,6-bis (chloromethyl)-4-pyrone

4-Chloroacetoacetyl chloride (14.8 g, 33.4 mol) in dichloromethane (35% strength solution) and scandium trifluoromethanesulphonate (1.45 g, 2.5 mol) were stirred at 25° C. for 6.5 days under a nitrogen atmosphere. Water (10 g, 0.55 mol) was then added and the organic phase was concentrated. 4.2 g of product were obtained (according to GC 68% crude product). After chromatography on a silica gel column, 0.7 g of pure product corresponding to a yield of 10.8% were obtained.

EXAMPLE 2

Preparation of γ-chloroacetoacetylmesitylene

4-Chloroacetoacetyl chloride (35% strength solution in dichloromethane, 26.2 g, 59 mmol), mesitylene (7.4 g, 59 mmol, and scandium trifluoro-methanesulphonate (2.6 g, 5.1 mmol) were introduced at 20° C. The reaction mixture was then stirred at 24° C. for a total of 2 days. It was then hydrolysed with water (10 ml). The organic phase was concentrated, and the residue was dried in a high vacuum. 9.1 g of crude product were obtained.

After chromatography on silica gel, 2.45 g of product (content of 67% according to GC) were obtained, which corresponds to a yield of around 11.7%.

What is claimed is:

1. A pyrone derivative of the general formula:

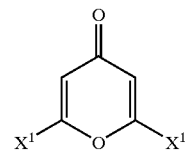

in which $X^1$ is halomethyl, with the exception of 2,6-bis (bromomethyl)-4-pyrone and 2,6-bis(dibromomethyl)-4-pyrone.

2. The pyrone derivative according to claim 1 in which $x^1$ is monochloromethyl.

3. A process for the preparation of pyrone derivatives of the formula:

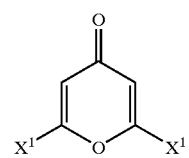

in which $X^1$ is halomethyl, characterized in that an acetoacetic acid derivative of the formula:

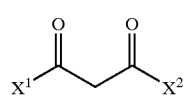

in which $X^1$ has the meaning mentioned above and $x^2$ is chlorine or bromine, is first treated with a Lewis acid and then converted into the desired product of formula I using water.

4. The process according to claim 3, characterized in that the Lewis acid employed is scandium trifluoromethanesulfonate.

5. The process according to claim 4, characterized in that the Lewis acid is employed in an amount from 0.01 to 3 mol per mole of acetoacetic derivative (II).

6. The process according to claim 5, characterized in that the reaction in the first stage is carried out in a halogenated organic solvent.

7. The process according to claim 6, characterized in that the reaction is carried out at a temperature of −20 to 60° C.

8. The process according to claim 3, characterized in that the Lewis acid is employed in an amount from 0.01 to 3 mol per mole of acetoacetic derivative (II).

9. The process according to claim 3, characterized in that the reaction in the first stage is carried out in a halogenated organic solvent.

10. The process according to claim 3, characterized in that the reaction is carried out at a temperature of −20 to 60° C.

* * * * *